United States Patent
Raghavan et al.

(10) Patent No.: US 6,549,803 B1
(45) Date of Patent: Apr. 15, 2003

(54) METHOD AND APPARATUS FOR TARGETING MATERIAL DELIVERY TO TISSUE

(75) Inventors: Raghu Raghavan, Baltimore, MD (US); Timothy Poston, Singapore (SG); Raju R. Viswanathan, Towson, MD (US)

(73) Assignee: Image-Guided Neurologics Inc., Melbourne, FL (US)

( * ) Notice: Subject to any disclaimer, the term of this patent is extended or adjusted under 35 U.S.C. 154(b) by 0 days.

(21) Appl. No.: 09/566,478

(22) Filed: May 8, 2000

(51) Int. Cl.[7] .................................................. A61B 6/00
(52) U.S. Cl. ........................ 600/431; 600/419; 600/407; 382/128; 382/131
(58) Field of Search .............................. 600/407, 419, 600/420, 431, 412; 250/302; 324/307, 309; 424/9.3; 604/264; 382/128, 131

(56) References Cited

U.S. PATENT DOCUMENTS

| | | | |
|---|---|---|---|
| 4,710,876 A | 12/1987 | Cline et al. | |
| 5,720,720 A | 2/1998 | Laske et al. | |
| 5,735,814 A | 4/1998 | Elsberry et al. | |
| 5,893,881 A | 4/1999 | Elsberry et al. | 607/5 |
| 5,925,066 A | 7/1999 | Kroll et al. | 607/3 |
| 5,964,705 A | 10/1999 | Truwit et al. | |
| 6,026,316 A | 2/2000 | Kucharczyk et al. | |
| 6,201,984 B1 * | 3/2001 | Funda et al. | 600/407 |
| 6,272,370 B1 * | 8/2001 | Gillies et al. | 324/309 |
| 6,352,683 B1 * | 3/2002 | ten Cate | 424/450 |

FOREIGN PATENT DOCUMENTS

EP 0468636 A1 6/1991 ............ A61N/1/30

OTHER PUBLICATIONS

U.S. patent application Ser. No. 09/532,145; filed Mar. 21, 2000; Applicant: R. Viswanathan et al.
U.S. patent application Ser. No. 09/532,667; filed Mar. 21, 2000; Applicant: R. Viswanathan.
U.S. patent application Ser. No. 09/532,037; filed Mar. 21, 2000; Applicant: R. Viswanathan.

* cited by examiner

Primary Examiner—Marvin M. Lateef
Assistant Examiner—Runa Shah Qaderi
(74) Attorney, Agent, or Firm—Mark A. Litman & Assoc. P.A.

(57) ABSTRACT

Movement of material in an organism, such as a drug injected into a brain, is modeled by a uniformly structured field of static constants governing transport by moving fluid and diffusion within the fluid. This supports planning of material introduction, (e.g., infusion, perfusion, retroperfusion, injections, etc.) to achieve a desired distribution of the material, continuing real-time feedback as to whether imaged material is moving as planned and will be distributed as desired, and real-time plan modification to improve results.

32 Claims, 7 Drawing Sheets

METHOD AND APPARATUS FOR TARGETING MATERIAL DELIVERY TO TISSUE

BACKGROUND OF THE INVENTION

1. Field of the Invention

The present invention relates to the delivery of material to tissue within a subject or patient. In particular, delivery of materials such as therapeutic, image enhancing, bio-active, pharmacological, nanotechnical or otherwise active materials is enhanced, particularly under real-time observable imaging systems (such as MRI, sonograms, and X-ray fluoroscopy). The invention further relates to the field of predictive mass transport or diffusion analysis for enhancing material delivery within a subject or patient.

2. Background of the Art

It is increasingly common to administer a drug or other material to a carefully targeted part of the body, rather than to insert it into the bloodstream and rely on some of it finding the target by carriage through the circulatory system. This targeted delivery has multiple advantages, when it can be performed effectively. Among the advantages of targeted delivery are that much less of the drug is needed, which itself represents a double gain. The drug itself is often costly, so reducing the volume of drug used in a treatment can represent a significant cost savings. It is also rare that any drug is wholly without negative effects ('side effects' with reference to the desired result). Where these adverse effects arise only where the drug reaches a specific non-targeted tissue, restricting the drug to a target that does not include that non-targeted tissue avoids the side effects completely. Even where this complete exclusion is impossible, the side effects may be far more acceptable if limited to a small region around the target, with reduced impact on the body at large, while delivering the desired result on the target tissue at full strength. Even where the side effects are not directly life-threatening, it can be important to avoid them: for example, to keep cancer chemotherapy drugs from the sites where they cause nausea and hair loss is good both for patient morale and for patient persistence in taking the drug. The importance of targeted delivery will increase for nanodevices (that is, devices with dimensions that are measured with one or two orders of magnitude of nanometers), which will often be designed for highly specific activity in a particular environment. Apart from the waste of resources in failure to reach the target site, their action in unintended (and less studied) sites may be hard to predict.

However, this format of targeted material delivery adds to the traditional complexity of computing dosage and delivery rates. Instead of a single figure of blood concentration, controlled by the rates at which the drug enters the circulatory system and at which it diffuses, flows and is absorbed, metabolized or excreted by various tissues, concentration becomes a distinct time-varying value (number) at each part of the body. Since the effects of a drug vary in complex ways depending upon local levels of concentration (scopolamine, for example, is an anti-nausea drug in a narrow range of levels), its administration must ensure that at active points in the target tissue the concentration is correct across the entire region of targeted tissue to obtain the desired effect, while at other non-active treatment points minimizing undesired effects (often, but not always, by minimizing concentration at such points). Planning delivery commensurate with desired treatment effects thus requires a difficult prediction task.

The need for such prediction of delivery and diffusion profiles has increased, particularly with the recent development of methods of tracking a diffusing or flowing material in real time in the patient (see U.S. Pat. No. 6,026,316) and with the advent of direct drug infusion techniques (see U.S. Pat. No. 5,720,720, which describes a catheter-based technique for high-flow microinfusion, and U.S. Pat. No. 5,735,814, which discusses drug infusion into brain tissue by means of an implantable pump and catheter). The physician can thus observe the changes in concentration in the various tissues around the entry point and delivery region, and modify plans according to observed events. It is important to note that the ability to modify or alter the significant results are not effectable instantaneously. Unlike an artist applying paint to a canvas, where the result is immediate, the physician must control the administration process according to events that will subsequently provide observable or therapeutic effects that result over a period of seconds or minutes. However, the decision itself must be immediate, so the prediction of consequences must be available immediately in advance of the alteration of procedures.

The physician's brain, or a computer in assistance, must model the concentration dynamics prospectively much faster than they occur in real time, to be useful in real-time decision making. However, current computational methods of predicting concentration dynamics in tissue take longer than the actual events in the process of delivery. These current methods rely on two steps, both of which are slow.

The first step, once a scan of the target region is available (in either preoperative or real time during initial steps of the medical procedure), is to build a structural model of the tissue structures present. This requires first the labeling of points according to the type of tissue present (this process is often called 'segmentation', since it categorizes the points into three-dimensional 'segments'). FIG. 1 illustrates this with a 2D slice of a brain scan, with the Globus Pallidus Medialis on each side extracted and marked visually (101) by a uniform gray shade. FIG. 2 shows the layered 3D region constructed from such slices. The planner then creates a best-fit geometric model of each structure present, such as bone, hippocampus, cortex, etc. FIG. 3 shows such a 3D model, for one of the segments identified in FIG. 1. Note that 'model' in this sense is a description of a geometrical shape, by (for instance) specifying vertices and faces, rather than a statistical model of a relationship, found by such methods as least squares. The decision as to what model fits the data best is somewhat heuristic: usually the objectives in fitting a geometric surface model to a bone are that points inside it should mostly be 'probably bone' on the evidence of local scan values, that they should form a connected region, that points immediately outside should be 'probably not bone', and that the surface should be reasonably smooth. (This last criterion tends both to reduce the impact of noisy data, and to allow a model that uses fewer vertices faces.) Methods for constructing such a surface model range from local definition of a surface that separates points according to whether they are above or below a threshold value, such as the Marching Cubes technique [W E Lorensen and H E Cline, System and method for the display of surface structures contained within the interior region of a solid body, U.S. Pat. No. 4,710,876] to active 'balloons' that move over the 3D image and attach themselves to boundary-like points, while resisting extremes of bending. (See for example L Cohen, L D Cohen, and N Ayache, "Using deformable surfaces to segment 3-D images and infer differential structures," CVGIP:19, Image Understanding 56(2):242–263, September 1992)

These models are divided into finite elements with simple geometric forms, such as tetrahedra (as in FIG. 3) or skewed cuboids, spheres or other geometric or mathematical shapes. On each such element, a partial differential equation governing concentration dynamics, which by the definition of 'differential' involves values at an infinitude of points, is approximated. This approximation is by a system of equations with a small or at least controlled number of variables. Typically each variable multiplies a fixed function of position before it is added to an approximation of the concentration function. In the simplest cases of current art, these functions may be constants and linear functions, such as functions proportional to x, proportional to y and proportional to z axes in the volume. In more complex approximations, they may be polynomial functions, wavelets, etc. The interactions between the scalar coefficients of these functions, within a finite element and between neighbors, are chosen to reflect the local rates of diffusion, flow, absorption, metabolism, excretion, etc., in a 'lumped' fashion over each finite element, so that the second step, computing the evolution of the approximated concentration function, gives results approximating those that would be predicted by a solution of the underlying partial differential equation.

The model-construction step is a relatively long procedure. It is not easily automated, and yet it must be complete before any predictions are possible. (FIG. 3 represents many hours of technical work.) Currently it takes much more time than would be acceptable in clinical practice, creating a delay between a preliminary scan and the administration of a drug. The scarce and costly expert labor required for performing this step is another obstruction to deployment. When the prediction is complete, the predictive calculations may still remain too slow for real-time guidance of the drug administration process.

The present invention exploits the new possibility of three-dimensional drug tracking, mentioned above, to create computational models of another kind, in a much more automatic way. Moreover, the equations can be solved rapidly enough for clinical use.

BRIEF SUMMARY OF THE INVENTION

The methods described in U.S. Pat. No. 6,026,316; and instruments used in U.S. Pat. No. 5,964,705 and copending U.S. Patent Applications bearing Ser. Nos. 09/532,145, 09/532,667 and Ser. No. 09/532,037 filed on Mar. 21, 2000, make it possible to administer a trackable material at one or more chosen points in the organism, and record the resulting change over time of the material's concentrations at a large number of points. From this information may be estimated the characteristic rates at which the tissue at these points permits the diffusion and other processes by which the concentration evolves. For example, if the concentrations at two neighboring points are always very similar, diffusion rates between those points must be larger than diffusion rates between nearby points where substantial differences in concentration persist. In quantifying these deductions or estimates, one must treat all the terms of the concentration dynamics simultaneously, since the action of each term of the concentration has had impact on the available data. These estimates may be refined by certain forms of a priori knowledge; for example, bone can be recognized by static aspects of the scan data, without reference to recorded concentrations, and diffusion and flow are known to be slow in bone. Using such scan data, with segmentation information where convenient, but without constructing a geometrical model specifically representing the segmented tissues, we construct a field of coefficients (such as direction-dependent diffusion rates, flow velocity of any fluid which transports the material, absorption rates, excretion rates, and any other processes important to the concentration dynamics). This creates a highly regular structure (e.g., FIG. 4, and FIG. 5) of data and evolution rules, varying from point to point only by the static local coefficients. We then model the evolution of the concentration either by a field of values (where the static local coefficients control the disappearance rate of the material and the interactions between neighboring concentration values), or by a population of moving particles whose probability of transfer between neighboring points, or of disappearance, is governed by static local coefficients. FIG. 6 illustrates this standard method-for the case of a 2D field evolving by diffusion only. A group of modeled particles starting at point 601 will spread out more rapidly into a dilute cloud than a group starting at point 602, if their motion is computed according to the constants in FIG. 5.

The creation of such data structures may be largely automated, following the flow indicated in FIG. 7. The process is computation-intensive, but can be greatly speeded by the use of parallel computing: an option is to use a highly pipelined machine such as a Cray mainframe computer, but—particularly with the rapid increase in machine speeds—a multiprocessor PC will suffice for an increasing portion of the functionality of the present invention. For a small fraction of the cost of the imaging device such as an MRI scanner that is providing the data, a chip or chipset optimized for this particular task will enhance the power of the images in guiding intervention. The automated process reduces delay and costs to levels acceptable for clinical deployment, and the concentration computations are of a type highly susceptible to computational speedup by parallelization methods, such as the use of pipelined vector architecture for a field of concentration values, or of 'single instruction multiple data' (SIMD) architecture to track a population of particles. This format enables computation to predict the results of particular administration strategies fast enough so that plans can be compared. An optimal plan can be chosen, in a clinically acceptable time. The plan can be implemented while the material administration procedure is in progress to track deviations from the expected evolution of concentrations, to deduce corrections in the static coefficients, and to offer both revised predictions of the results of the current strategy and predictions of possible alternative strategies. All of this may be done in time to be useful to the controller.

DETAILED DESCRIPTION OF THE INVENTION

In the practice of the present invention, a region of the body is treated as a field P of local properties such as diffusion and absorption constants, rather than as an assembly of organs. We follow the convention that a 'field' is a specification, at each point in a domain, of a scalar, vector or tensor quantity characterizing a property, or of several such: the value of P at a point x is the ordered list of local property values at x. This field may vary in time (for instance, with heart or lung motion) as well as in space. Affected by this field, but taken as without influence on it, is a velocity field v of moving fluid. This moving fluid may in some cases be a steady or periodic motion due to bodily processes, but in many cases of interest the velocity field is more often a transient, time-varying flow driven by a pressure difference between insertion devices, concentration variations, osmotic pressure, and background pressure in the organism. At some stage after insertion ceases or release of the material ceases, the flow velocity v may become negligible. Finally, one object of interest is the concentration field C of the concentration of a diffusing material such as (but not restricted to) molecules, particles, globules, a dispersed or suspended phase, cells or microscopic devices, dissolved or in suspension in the moving or static fluid. In some cases of interest for the invention, this field varies in time. In one implementation, we treat the concentration as influenced by, but without influence upon, the fields P of local properties and v of flow velocity. One method of the invention is (a) to estimate P, (b) to estimate v, and (c) to use these estimates to predict the evolution of C, and (d) to use this capability of prediction for various purposes of medical or biological utility. In certain cases, an impact of C upon P or v (for instance, where a diffusing drug stimulates a change in the mechanical properties of tissue) requires an iterative process of improving the estimate (a) or (b) in the light of the results of (c), using the result for a repeat of (c), and so on.

Figure 4:
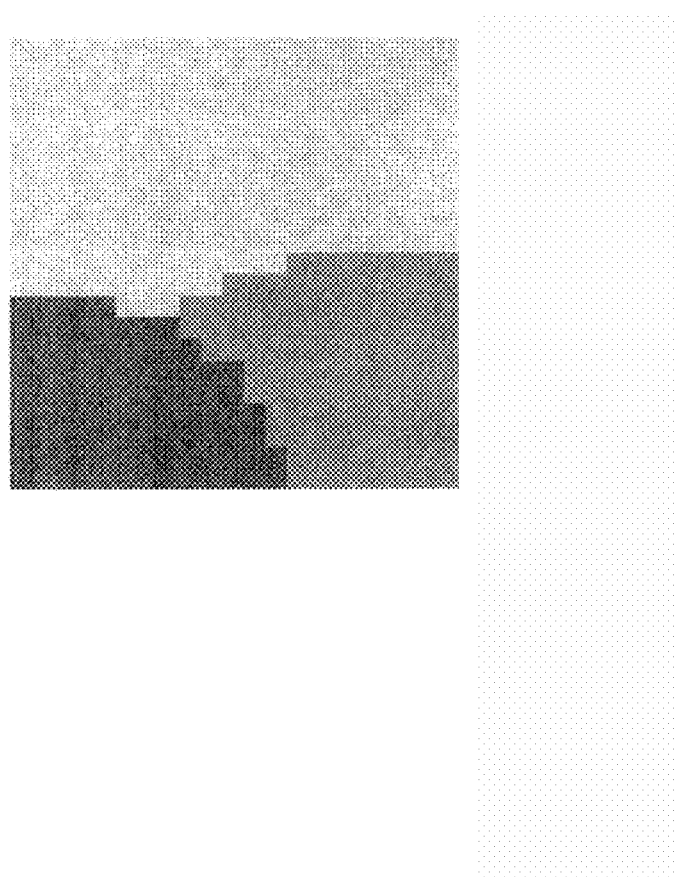
FIG. 4. A regular 2D grid of scan samples, representing the 3D analogue, each of which is shown with a gray shade corresponding to its classification as to tissue type.
Figure 5:
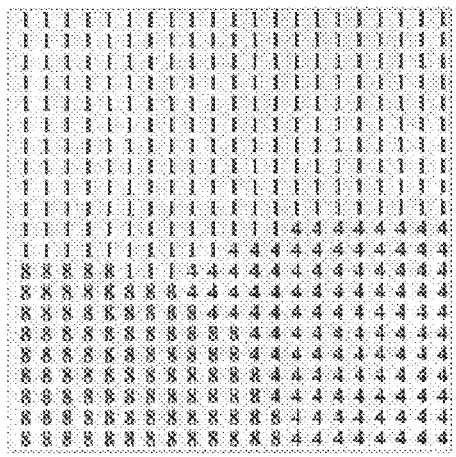
FIG. 5. A regular 2D grid of points, representing the 3D analogue. To each point are assigned coefficients corresponding to its type (as shown in FIG. 4) for the various processes by which the material of interest is transported or is removed from the system; for simplicity, a single coefficient is shown.

The estimation (a) of P may be done in any manner. At least two ways will be specifically described. A first method is to use scan data to classify ('segment') each point in space as belonging to the specific tissue type for which the scan value found there is characteristic, and to assign corresponding coefficient values based on pre-established knowledge of that type of tissue. Such assignment is illustrated (in 2D analogue) in the transition from FIG. 4, which shows points classified by tissue type and visualized by distinct gray levels (or color levels or vector symbols), to the data structure in FIG. 5, which shows diffusion constants associated with the tissue type at each point. (In general, more than the single number shown is necessary to encode the various parameters forming part of P.)

In some cases, the segmentation process can be improved by smoothing or otherwise processing the raw data or mathematical models, or even by constructing best-fit geometric models of the segments or such boundaries as the surface where tissue meets a fluid-filled ventricle, to enforce agreement with such a priori knowledge about a segment's shape as that the outer membrane of the cerebral cortex is a folded surface without holes and without tubes connecting parts of it, but such geometric models are incidental to the present invention. With the current low speed and degree of automation of such models, they do not at present form part of a preferred implementation.

A second example of a way to estimate P is to inject material (e.g., scout or testing material, MRI field modifying, sonogram enhancing, inert materials, etc.) whose concentration is detectable in a scan. The field of densities is then detected as a function of position and time, and the properties computed directly from the changing values detected. Since these changes in C are affected also by non-negligible values of v, we describe techniques for such computation in a later section.

Similarly, for step (b), v may be estimated in several ways. One way is, again, to begin with a segmentation, and to provide an equation assumed or estimated to govern the flow, with terms in the equation for the effects of the tissue it is flowing through. With the assumption of an incompressible fluid (usually appropriate when a diffusing drug is injected, though less exact for lung air through which an anesthetic diffuses), fluid transport is governed by $$\phi\left(v - \frac{\partial u}{\partial t}\right) = -K \cdot \nabla(\phi p) \tag{1}$$

where at a particular point x of the tissue the value $\phi(x)$ is the pore fraction, $p(x, t)$ is the (spatially and temporally varying) fluid pressure, $K(x)$ is the tensor of hydraulic permeability, and $u(x)$ is the spatial displacement of that point of the tissue under the forces from the flow.

The quantities v, u and p are solved for collectively, using boundary conditions such as that far from the injection site, p has its background value for the organism. Equation (1) cannot of course be solved alone: for quasi-steady flow (negligible acceleration) we have the force balance equation $$\nabla \cdot (C \cdot \epsilon) - \nabla(\phi p) = 0 \tag{2}$$

where C is the tensor of constitutive moduli for the tissue and $$\epsilon = \left[\frac{1}{2}\left(\frac{\partial u_j}{\partial x_i} + \frac{\partial u_i}{\partial x_j}\right)\right]$$

is the tissue strain tensor. (If the pore fraction $\phi$ is modified by change in pressure, an equation for this influence on equation (2) must be added.) We require also the effective continuity equation $$\nabla \cdot (\phi v) + \nabla \cdot \left[(1 - \phi)\frac{\partial u}{\partial t}\right] = \Omega, \tag{3}$$

where $\Omega$ is determined by the net rate $F_v$ of fluid loss from blood vessels into the tissue per unit tissue volume, and the absorption rate $F_l$ of fluid by lymphatics per unit volume of tissue.

Numerous modifications to these equations will be apparent to those skilled in the art. Mathematically modified, situationally modified, structurally modified, compositionally modified, environmentally modified or otherwise functionally modified equations or algorithms can be used in the practice of this invention, and these modified equations are assumed and intended to be included within the recitation and description of these equations or algorithms except where the term "consisting of" directly precedes the equation or algorithm. For example, if the diffusing substance is physiologically active, it may modify the pore fraction $\phi$ (and hence the hydraulic permeability K) by causing cells to change shape, or the fluid loss rate $F_v$ by constricting or relaxing the blood vessels. if the tissue is sufficiently rigid, we may neglect the force balance equation (2) and reduce transport to $$\phi v = -K \cdot \nabla(\phi p). \quad (4)$$

A potential result of this invention is not to give a universal system of equations governing transport in tissue, or indeed a universal approach to solving such equations, but to explicate a method that integrates such equations and solution methods into a system for interactive simulation. We will illustrate the method using equations (3) and (4). In this case the field of properties P would be the collective name for $(\phi, \Omega, K)$. In other instances it would include (for instance) the tensor C of constitutive moduli for the tissue, the local coefficients governing the influence of the concentration C on pore fraction $\phi$, and so forth.

Figure 1:
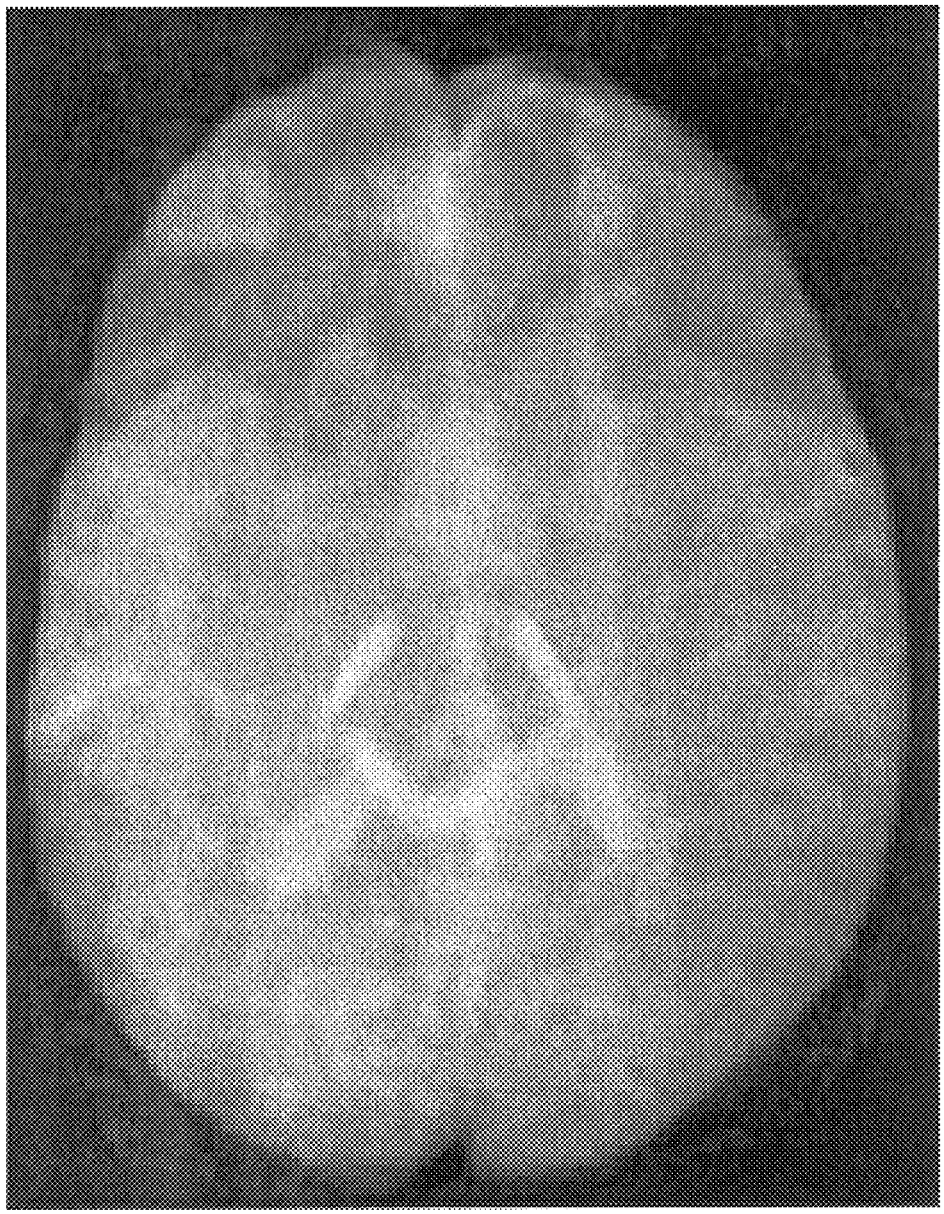
FIG. 1. A 2D scan image, representing the 3D data actually available, in which a particular tissue (the Globus Pallidus Medialis or GPm, shown uniform gray) has been identified.
Figure 2:
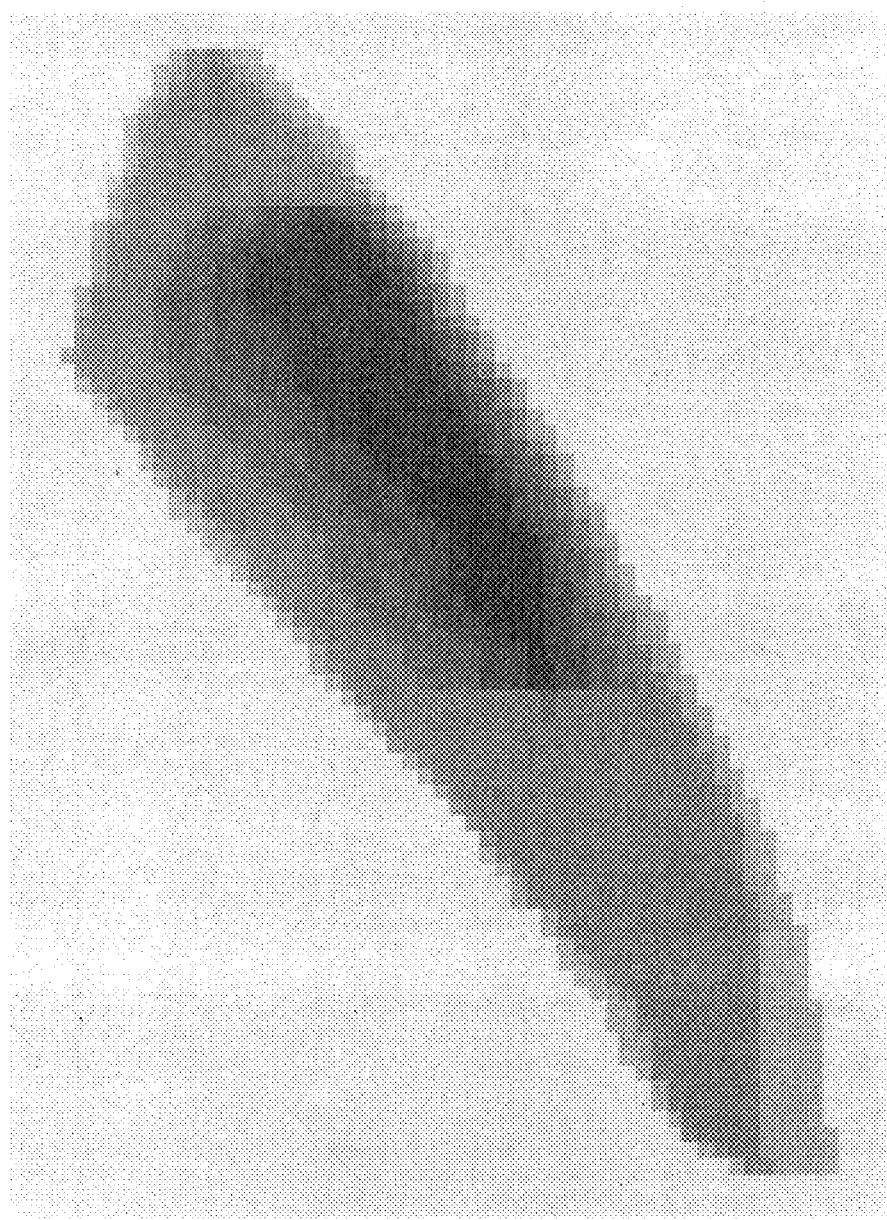
FIG. 2. The 3D form of the GPm in the same patient, built from slices like those in FIG. 1, as an unstructured volume.
Figure 3:
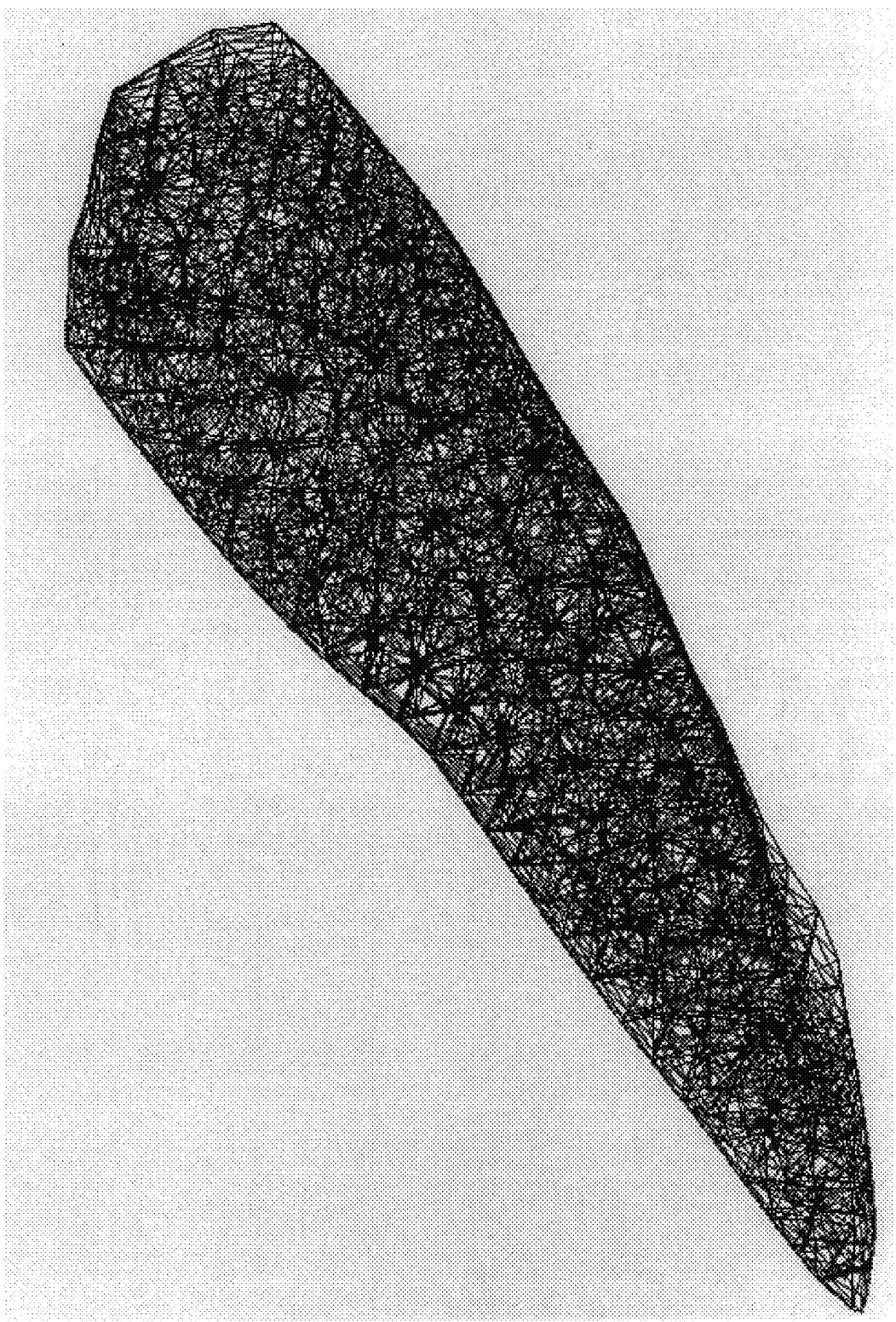
FIG. 3. The 3D region shown in FIG. 1, divided into geometric elements on which concentration variation may be approximated by a weighted sum of a small set of standard functions.

The values of fields such as K and $\phi$ (or, if necessary, their dependency laws on other quantities in the equations) can typically be taken from pre-established knowledge of the properties of different tissue types, though these values may also be derived from 'scout' injections or revised in the light of incoming data during a procedure. The equations may be solved to find v by a variety of (mostly approximate) numerical methods, given boundary conditions specified by a plan to inject material at a given forced rate of flow, perhaps time varying, or at a given pressure differential, perhaps time varying, over the background internal pressure of the body. Equations may also be influenced by specific blood factors and properties and conditions, and data from blood tests or other physiological tests may be used to modify the equations. The tests may be performed before or during the procedure, and certain tests may be performed outside of the patient for determining modification functions or modified constants based upon those blood properties. The equations may also be modified for convenience in approximate solution. For example, the partial differentials $\partial/\partial x_1$, $\partial/\partial x_2$ and $\partial/\partial x_3$ applied to each quantity q (standing for u, v, etc., as appropriate) may be replaced by the respective partial difference operators $(q(x_1+\text{step},x_2,x_3)-q(x_1,x_2,x_3))/[\text{step}]$, $(q(x_1,x_2+\text{step},x_3)-q(x_1,x_2,x_3))/[\text{step}]$ $(q(x_1,x_2,x_3+\text{step})-q(x_1,x_2,x_3))/[\text{step}]$, and time derivatives similarly replaced by time difference operators. This creates a system of equations involving only values at a finite set of grid points at a finite set of times. Such a system S may be solved by (for instance) taking an initial estimate, approximation or guess for the value of each adjustable quantity at each grid point, computing the nearby partial differences, assessing the failure to satisfy S at that point, adjusting each scalar in the direction of satisfying S better, and repeating the process for the adjusted values. (The amount by which to change the values at each step, for convergence to a solution and rapid convergence to a solution, is the subject of a large section of the Numerical Analysis literature.) Alternatively, the region in which the system S is to be solved may be subdivided into smaller regions, on each of which each quantity q is approximated by a linear combination $c_1 q_1 + c_2 q_2 + \Lambda + c_M q_M$ of a finite collection of M standard basis functions, which may be polynomials, wavelets, or other mathematically useful forms: integrating the system S over a sub-region gives a system S of equations relating the unknown coefficients $(c_1, c_2, K, c_M)$, rather than the point values of the quantities q. (Solution for each subregion, on which the functions of interest in the differential equation require an infinity of values for full specification, is thus reduced to determining a finite set of coefficients. Such techniques are therefore often called finite element methods. The current drug diffusion modeling techniques, described above, depend on determining anatomy and dividing particular tissues into finite elements, like the tetrahedron shown in FIG. 3. It is an essential feature of the present invention that we do not depend on this, though we may use automated methods to fit a finite element decomposition to the continuous fields of quantities q.) The system S may then be solved by iterative adjustment from an initial guess, or otherwise.

A second approach to performing step (b) is to inject comparable fluid, which is visible in some way to a scan (as by MRI, sonogram, X-ray fluoroscopy, etc.), track its motion without assumptions concerning pressure, viscosity, etc., and derive the coefficient values governing its evolution from the evolution observed. (This 'scout' process may be combined with that for diffusion coefficients: see below.) Scan data are not necessarily sufficient to imply values for all dynamical variables. Motion being easier to observe at a distance than is pressure, it is usually necessary here to specify boundary conditions imposed by the background and the injection device and solve an equation such as (1) or (3) together with (2) above, for the tracked v and appropriate boundary conditions on pressure p, as an equation in the less directly observed quantities p and K. (If (1) is replaced by an equation with more variables these are desirably included in this process.) For different injection plans, equation (1) can then be solved to find v, as in the first approach to step (b). The visibility of the fluid to a scan may be a result of the detectability of material dissolved or suspended in the fluid, if it is able to move freely with the fluid (rather than be filtered, as would occur with large particles or with $CO_2$ bubbles, the latter having an excellent visibility to ultrasound), or imposed by the scanning method itself, such as the use in magnetic resonance imaging of preparing the hydrogen nucleus spins in some regions differently from those in others, so that the movement of the regions may be tracked.

A third approach to step (b) exploits the real-time tracking of the material of final interest or the surrounding fluid, where naturally or by modification it is visible to the scanning method used. This provides data from which the current v may be derived without assumptions concerning the determining physics. Unless the flow is constant, however, prediction of future values requires estimation of the equation coefficients, as in the previous case. Such estimation involves solution of a boundary value problem fast enough to use the coefficient values in a boundary-value computation of predicted v, which to be relevant must be in a time short compared to the injection process. This places higher demands on computing power.

The prediction (c) may be performed by a variety of numerical solution methods, employing an already well-developed art. At the level of the continuum approximation (where the finite number of diffusing particles is represented by an infinitely subdivisible range of concentration values, varying continuously from point to point) diffusion of a molecular substance X may be governed by an equation $$\frac{\partial C}{\partial t} = \nabla \cdot (D \cdot \nabla C) - \nabla \cdot (vC) + \frac{1}{\phi}[F_s - F_{ls} - R_{bind}(C, B)] \quad (5)$$

where D is the diffusion tensor and the last term includes rate of addition of X molecules (if any), $F_s$ from blood vessels into brain tissue, rate of removal $F_{ls}$ of X molecules by lymphatic drainage, and $R_{bind}(C,B)$ is a kinetic term which accounts for the reaction of X molecules with compounds fixed in the tissue, such as binding receptors. These rates are normally reported per unit volume of tissue; consequently we need the factor $(1/\phi)$ in front of the last term in order to convert to a rate per unit fluid volume. If the substance X resists passage through the blood-brain barrier and does not react with the tissue, (5) reduces to $$\frac{\partial C}{\partial t} = \nabla \cdot (D \cdot \nabla C) - \nabla \cdot (vC) \quad (6)$$

or for diffusion in static fluid, $$\frac{\partial C}{\partial t} = \nabla \cdot (D \cdot \nabla C) \quad (7)$$

which we will use for illustration below.

Figure 6:
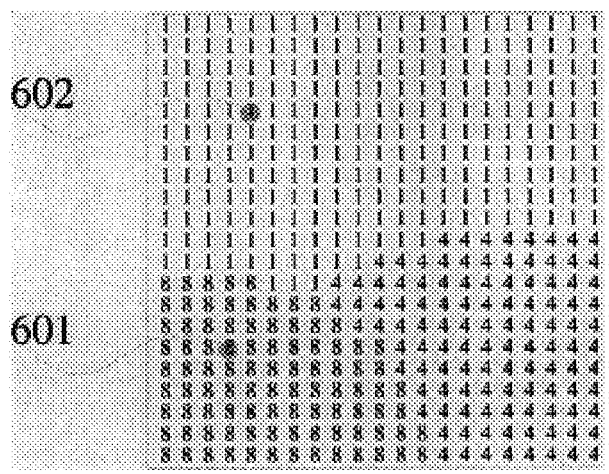
FIG. 6. A randomly-moving particle at point 601, where according to FIG. 5 the diffusion constant is high, is modeled as more likely to move to a neighboring point than a particle at point 602, where the constant is low.

Still another alternate type of model approximates the very large collection (order $10_{23}$) of real diffusing particles by a much smaller set of numerically simulated particles, each one moving probabilistically on a grid of points. In a time step $\Delta t$, a particle's probability of jumping from a point to a neighboring point $\tilde{x}=x+\delta$, separated from it by the vector $\delta$, is proportional to $\exp(-y^T D^{-1} y/2\Delta t)$, where $y=(\delta-v\Delta t)$ and $D^{-1}$ is the inverse of the matrix D. FIG. 6 illustrates this for the field of diffusion constants shown in FIG. 5; a particle at point 601 is more likely to jump, given a diffusion constant of 8.0, than a particle at point 602. Consequently, a set of particles injected at point 601 will spread out faster than a set at point 602. The gradient operator $\nabla$ applied to C in (ref: static diffuse) corresponds to averaging the net flow between x and $\tilde{x}$ (where x currently has more particles than $\tilde{x}$, independently jumping, more particles jump from x to $\tilde{x}$ than from $\tilde{x}$ to x), and the divergence operator $\nabla \cdot$ corresponds to summing the difference of jump rates into and out of x on opposite sides, in each direction. Loss and binding effects are included by terms that govern a particle's probability of disappearing or becoming bound or freed; infusion at given rate is modeled by the creation with controlled frequency of new particles to be tracked. Such particle models are a well-known field of study (see, for instance, Donald Greenspan, 'Particle modeling', Birkhäuser, Boston, 1997), and their solution may be summarized as "follow the particles and see how many end up where."

The choice of a concentration-oriented model like (5) versus a probabilistic particle model is dictated less by theoretical considerations than by available computing machinery. Any computer with pipelined vector architecture, such as the machines in the Cray series, performs particularly fast on an array of concentrations, densities, etc., while a large system of less closely coupled processors operating in parallel may run fastest by allocating one or several particles to each.

Either class of system can be optimized at the hardware level to create a computer dedicated to the fast solution of the particular class of problems arising in solution of concentration problems and coefficient estimation of the kinds necessary for this invention. The use of such hardware-optimized components in a clinical implementation forms part of a preferred implementation, subject to economic feasibility.

Coefficient Estimation Methods

The first step in estimating coefficients is to exploit a priori knowledge of tissue types. For example, the high density of bone cortex, clearly apparent in CAT scans, is associated with effectively-zero diffusion and permeability tensors for the fluids and diffusing substances chiefly of interest here. These values may be assigned to the corresponding points in the grid of values for these tensors, with a high degree of confidence. This confidence level is itself recorded for these points, in an associated field of data that may be discarded once the estimate is complete.

At other points, scan data are less determinative. For example, at the surface of the cerebral cortex is a membrane with very low permeability, so that there is little diffusion across it. The membrane itself is rarely visible in scan data such as MR images. In some parts of an image, its existence can be deduced by the presence of a boundary between cortical tissue and cerebrospinal fluid, so that a suitably tuned edge detection filter can assign low permeability to surface points with a high associated confidence level. However, where two parts of the cortex are pressed together in a sulcus (fold), no local operator on typical current MR data can detect the existence of a boundary. The human observer may see that a membrane must be present, and approximately locate it, by continuation from other parts of the image; but human input of such perception and reasoning is too labor-intensive for a clinical application. As described in the Background, work exists on three-dimensional 'virtual balloons', computed objects which fold themselves to fit the available data and stretch across such gaps in local evidence, with analogous results to human interpolation, but this is not yet routinely usable at clinical speeds. Where such techniques become available, implementations of the present invention may import data from the resulting models of tissue structure, but this is not part of the preferred first implementation. Other intelligence input may also be used, such as with touch screen functionality, light wand functionality, or other user or automatic functionalities to add line features, surface features, volume features or composition (property) features to a model or even equations.

In certain cases it will be essential to perform 'scout' injections, with diffusing material whose concentration $C(x_1,x_2,x_3,t)$ can be tracked over time in three dimensions. Taking as an example the static case, where (7) can be used alone, its use requiring us to determine the symmetric diffusion tensor $$D = \begin{bmatrix} d_{11} & d_{12} & d_{13} \\ d_{12} & d_{22} & d_{23} \\ d_{13} & d_{23} & d_{33} \end{bmatrix} \quad (8)$$

in a region of interest (either spatially constant or varying from one grid point (i,j,k) to the next, as the phsyical situation requires). If C has by notation the estimated value $C_{ijkt}$ at time t, then pointwise, the vector $\nabla C$ may be approximated by $(C_{(i+1)jkt} - C_{ijkt}, C_{i(j+1)kt} - C_{ijkt}, C_{ij(k+1)t} - C_{ijkt})$, so that (7) gives us the discrete analogue $$\frac{C_{ijk(t+\Delta t)} - C_{ijkt}}{\Delta t} = \left( [d_{11} \quad d_{12} \quad d_{13}] \begin{bmatrix} C_{(i+1)jkt} - C_{ijkt} \\ C_{i(j+1)kt} - C_{ijkt} \\ C_{ij(k+1)t} - C_{ijkt} \end{bmatrix} - [d_{11} \quad d_{12} \quad d_{13}] \begin{bmatrix} C_{ijkt} - C_{(i-1)jkt} \\ C_{(i-1)(j+1)kt} - C_{(i-1)jkt} \\ C_{(i-1)j(k+1)t} - C_{(i-1)jkt} \end{bmatrix} \right) +$$

$$\left( [d_{12} \quad d_{22} \quad d_{23}] \begin{bmatrix} C_{(i+1)jkt} - C_{ijkt} \\ C_{i(j+1)kt} - C_{ijkt} \\ C_{ij(k+1)t} - C_{ijkt} \end{bmatrix} - [d_{12} \quad d_{22} \quad d_{23}] \begin{bmatrix} C_{(i+1)(j-1)kt} - C_{i(j-1)kt} \\ C_{ijkt} - C_{i(j-1)kt} \\ C_{i(j-1)(k+1)t} - C_{i(j-1)kt} \end{bmatrix} \right) +$$

$$\left( [d_{13} \quad d_{23} \quad d_{33}] \begin{bmatrix} C_{(i+1)jkt} - C_{ijkt} \\ C_{i(j+1)kt} - C_{ijkt} \\ C_{ij(k+1)t} - C_{ijkt} \end{bmatrix} - [d_{13} \quad d_{23} \quad d_{33}] \begin{bmatrix} C_{(i+1)j(k-1)} - C_{ij(k-1)} \\ C_{i(j+1)(k-1)} - C_{ij(k-1)} \\ C_{ijkt} - C_{ij(k-1)} \end{bmatrix} \right)$$

$$= \begin{bmatrix} d_{11} \\ d_{22} \\ d_{33} \\ d_{12} \\ d_{13} \\ d_{23} \end{bmatrix}^T \begin{bmatrix} C_{(i-1)jkt} + C_{(i+1)jkt} - 2C_{ijkt} \\ C_{i(j+1)kt} + C_{i(j-1)kt} - 2C_{ijkt} \\ C_{ij(k+1)} + C_{ij(k-1)} - 2C_{ijkt} - \\ 2C_{ijkt} + C_{(i-1)jkt} + C_{i(j+1)kt} - C_{(i+1)(j-1)kt} + C_{i(j-1)kt} - C_{(i-1)(j+1)kt} + C_{(i+1)jkt} \\ C_{(i-1)jkt} + C_{(i+1)jkt} + C_{ij(k+1)t} - 2C_{ijkt} - C_{(i+1)j(k-1)t} + C_{ij(k-1)t} - C_{(i-1)j(k+1)t} \\ C_{i(j-1)kt} - C_{i(j+1)(k-1)t} + C_{ij(k-1)t} + C_{ij(k+1)t} - C_{i(j-1)(k+1)t} + C_{i(j+1)kt} - 2C_{ijkt} \end{bmatrix}$$

$$= [d_{11} \quad d_{22} \quad d_{33} \quad d_{12} \quad d_{13} \quad d_{23}] \begin{bmatrix} \hat{C}_{ijkt}^{11} \\ \hat{C}_{ijkt}^{22} \\ \hat{C}_{ijkt}^{33} \\ \hat{C}_{ijkt}^{12} \\ \hat{C}_{ijkt}^{13} \\ \hat{C}_{ijkt}^{23} \end{bmatrix} = d\hat{C}_{ijkt} \text{ for short.}$$

Catheters with multiple lumens could be particularly useful in this practice. A first scout injection could be released through one lumen and the tracking/diffusion parameters determined. The actual active material may then be released through a second lumen (or the first lumen purged or emptied before administering the active material through the first lumen).

For each time step we have values for $C_{ijkt}$ and its neighbors, and hence for the vectors $\hat{C}_{ijkt}$, giving an instance where (7) is assumed approximately true. Given (for example only) six such instances, if the $\hat{C}_{ijkt}$ are linearly independent, this suffices in principle to determine d and hence D uniquely. A similar process (requiring more instances) can provide estimates of a larger set P of parameters, such as D and K together. Where v is being estimated the algebra is largely similar, but can be separated from the estimation of D because fluid motion leads to transfer of concentration which is antisymmetric between neighbors (transferring from one point to another), where the diffusion analysis above finds the symmetric influences on transfer.

In practice, given the noisiness of data, it is better to find a least squares estimate (or other linear or exponential approximation) for D, using all available instances of $\hat{C}_{ijkt}$ whose entries are non-negligible; and it is useful to smooth the data C before entering this process. (The smoothing is best weighted by values from an edge operator applied to the background CAT, MR or other image data, since where there is evidence of sharp transition in the tissue, smoothing away sharp differences in C is more likely to introduce error.) Other refinements of this estimation process will be obvious to those skilled in the art. With digital imaging concurrent with the procedure, pixel-based smoothing or blending are examples of modalities for assessing or reflecting tissue transition. Edge feature sharpening techniques are more specific examples of such image enhancing treatment to reflect such tissue transitions.

Where other solution methods for predicting C are preferred to direct manipulation of values $\hat{C}_{ijkt}$, or for other reasons as they arise, this estimation step may be performed by analogous but non-identical techniques, clear to those skilled in the art. For example, if a quantity q as described above is approximated by combinations $c_1q_1 + c_2q_2 + c_2q_2 + K + C_M q_M$ of basis functions, estimation from data of coefficients in the equation used to predict the evolution of the $c_i$ may give more robust results than estimation of pointwise values for parameters such as D. Such modifications fall within the scope of the invention here claimed, which primarily addresses the exploitation of any estimation method in creating a full system for prediction and control.

The condition above that the $\hat{C}_{ijkt}$ should be linearly independent is not a trivial one. Six randomly sampled vectors from a 6-dimensional space are likely to be independent, but the samples here are not drawn randomly. In particular, if the medium is isotropic and the diffusing material spreads from a single point α, differences in simultaneous C value at two points x and y equidistant from α will typically represent only noise. Such data cannot directly reveal constants governing diffusion tangent to a sphere centered on α. However, the degeneracy of the estimation problem itself provides evidence of isotropy. For example, diffusion in an anisotropic medium generically has level sets of concentration that pass through a given point x in different directions at different times. The estimation procedure can thus be reduced to fitting D as a scalar multiple of the identity matrix, for which the data will be sufficient.

Various forms of a priori knowledge can strengthen this estimation process. For example, where (as with bone) a diffusion tensor D can be assigned with a high confidence value from the static image background alone, a lower variance in the least squares fit to D should be required in modifying the estimate away from that assignment. In other case it may be known that a tissue type is anisotropic with characteristic diffusivities in high and low directions, but the direction of highest diffusivity may not be deducible from the static background image. In this case, we would use the scout data (or incoming data as a plan is being executed) to estimate the orientation of D at each point. Estimating only the three degrees of orientation freedom, with the eigenvalues assumed known, can be more robust.

Predictive control

Image guidance permits a user injecting a substance to place a delivery instrument such as a catheter into (for example) a human brain, and see where it is located relative to scan-visible structures. In present practice, the user makes a plan for injection, determining the quantity of the substance to be loaded into the delivery system, the pressure or flow rate (perhaps variable) at which the substance is to be injected, and the time over which the flow is to be maintained. The objective of such a plan is to deliver the substance in desired quantities in or to 'target' tissues, often while minimizing the amount delivered to non-target tissues (where it would be wasted) and to vulnerable tissues where the substance would do harm. It is also desirable to limit excess pressure, and the resulting edema (swelling) of tissue, in spatial extent, intensity and duration.

Commonly, the plan is entered into a computer that will control the injection process, but direct hand control is also possible. This plan is then followed, with a change only if visually inspected images (e.g., U.S. Pat. Nos. 6,026,316; and 5,964,705) of the diffusing substance makes clear that concentration, pressure or edema is not following the course expected by the user. Since the evolving concentration is a 3D scalar field in the midst of complex 3D structures, visual inspection requires a strong grasp of the 3D relationships revealed by scan data. Current 3D display techniques do not display these relationships clearly enough to guarantee fast comprehension and appropriately swift action by the medical user. It is rare that undesired consequences are seen fast enough to limit their scope.

The present invention replaces or augments such visual inspection by enabling the computer to enter this part of the control loop. At the simplest level of control in the present invention, the user chooses a position or target area, and specifies an injection plan (quantity, duration, pressure/flow-rate) to the computer. In the novel process provided by the present invention, the computer then solves or determines the transport properties on the assumption that this plan is followed, using the field of parameters P established as above together with available subsidiary data such as blood pressure to specify boundary conditions. The system displays the predicted values of concentration, pressure and edema, and the user has the opportunity to examine them at non-crisis speed and determine whether they are satisfactory. If not, the user repeatedly changes the device position (actually or virtually) and/or the specified plan, until an acceptable result is predicted. At this point, the plan is implemented under computer control.

At a more strongly supported level of control, the user specifies target tissues by marking them (for example, by using a 2D or 3D mouse or other input device such as a joystick to click on points, specifying ball-shaped regions of adjustable radius; or, outlining a target region; or, moving a 2D or 3D cursor through an image of the region of interest and seeing a resulting spray-can-like superposed image showing the intensity of target values as input for corresponding points; etc.). Minimum and maximum target concentrations, and limits on pressure, edema and their durations may be input separately. Similarly, the user may mark vulnerable tissues, and quantify their vulnerability. The user inputs a plan as above, and the computer predicts the resulting concentrations. In this mode, the computer display includes markers for agreement with the user's goals, so that visual inspection is guided to possible regions of concern. When a chosen plan is implemented, using scan-visibility of the injected substance the computer can monitor deviation from the expected time course of concentration, and detecting problems earlier (and thus more usefully) than visual monitoring. Where deviation beyond a threshold level is detected, the computer derives revised estimates for the transport parameters P and deduces revised predictions for the results of the plan. If these involve values pre-specified by the user as unacceptable, the computer may pause the injection for new user input. If they are acceptable, the computer may then implement the procedure.

At a higher level again, where the computer is capable of carrying out multiple predictive simulations of transport in available time, the computer may search the space of possible plans for the plan(s) with the result most quantitatively desirable according to the user-specified criteria. (For example, it may begin with a heuristically chosen starting plan, perhaps a standard one, investigating the predicted result of successive changes in the plan, making those changes with improved results. In general the physics will not allow exact achievement of a particular user-specified target concentration, so this is not well-posed as an inverse problem. The system's goal must be to find a plan whose results are within user-specified limits) Such plan(s) may be presented to the user, to be accepted or rejected by keystrokes, mouse click, voice, or other input means devoid of quantitative detail; or, the user may quantitatively modify the plan(s), view the consequences of each modified plan, and select among this larger set.

Where the computer is thus capable of generating plans adjusted to user goals, when monitoring the real injection reveals a deviation from the expected concentration changes the computer may not only deduce corrections to the assumed parameter field P, create revised predictions and providing a warning if the results are unacceptable, but find a revised plan with more satisfactory results and (subject to user approval, or autonomously) implement the revisions while the injection is in progress. This variant of the invention requires the greatest speed, and is the most likely to require implementation with dedicated hardware optimized for the purpose of solving the necessary equations fast.

Flow of the Method

Figure 7:
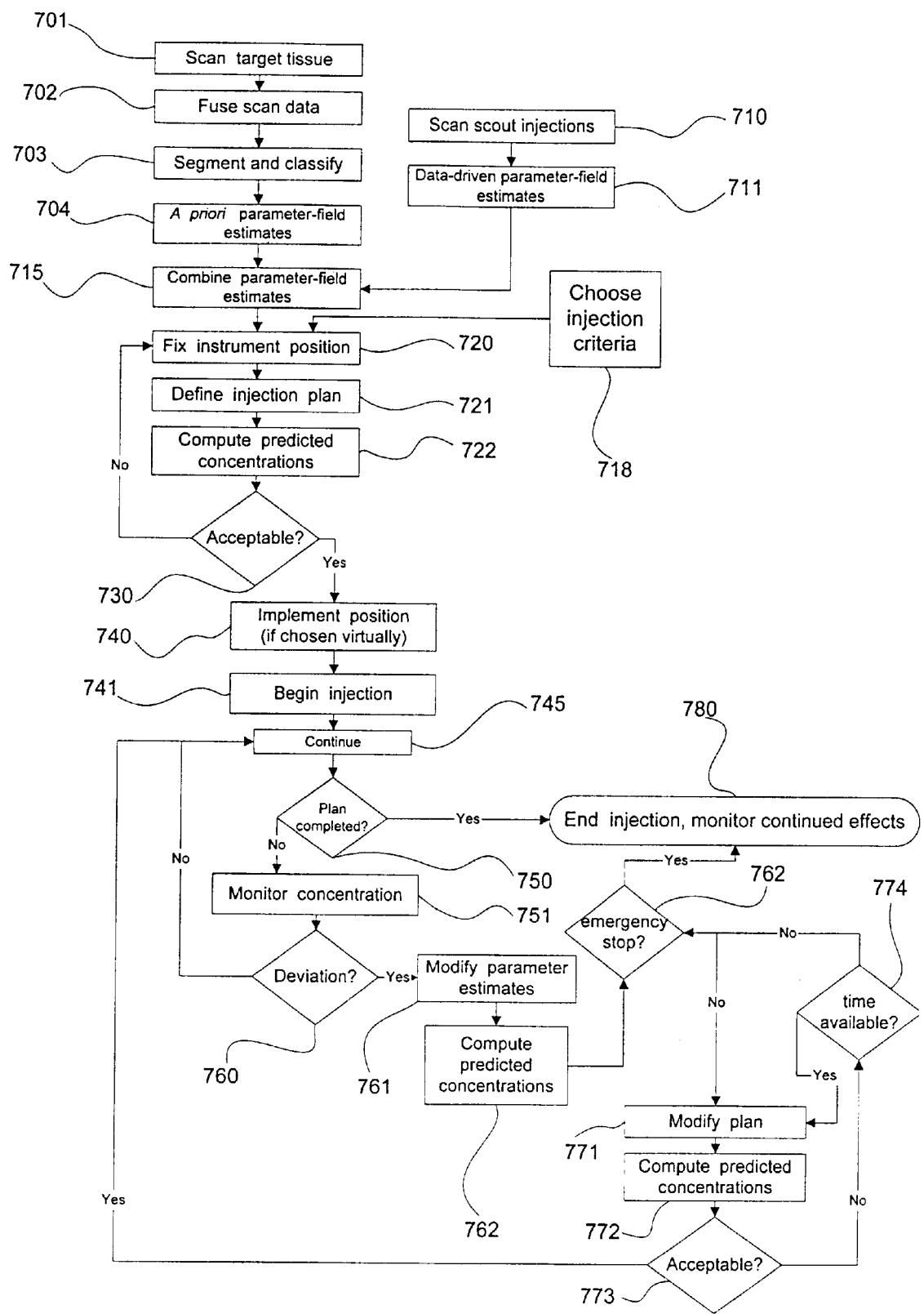
FIG. 7. The flow chart of the computation and interaction procedure of the invention.

In summary, FIG. 7 shows a logic of the present invention. First, the target tissue is scanned (701), using one or more 3D imaging modalities such as CAT, ultrasound, functional magnetic resonance, etc. For more than one modality, the data may be brought (702) into a shared coordinate frame. Using the resulting information about tissue properties at each point in the scanned region, the points are classified into tissue types (703) and assigned transport parameter values according to the general properties of these types (704). In some cases this provides sufficient information about transport properties in such tissue of the material to be injected. Commonly, the user will also perform scout injections and scan the resulting changes in concentration of the same or a similar material (710). This will thereby derive (711) estimates more specific to the patient, for the subregions in which the scout injections provide robust data, as attested by low measures of noise. These two estimations of parameter fields are merged (715), each point's parameter values being more strongly influenced by the more confidently derived estimate at that point, and sharp changes being more acceptable where there is evidence from any modality of a boundary.

The planning specific to the injection begins with choosing regions that should receive the injected substance, or that are vulnerable to it (718), and limits on allowable pressure and edema. This may be in the mind of the user, setting the mental stage for later decisions, or input to the computer by means of a graphical interface. The user or in some implementations the computer then fixes a position for the instrument used (720), which at this stage may be either a physical image-guided process or a virtual placement within a displayed scan image. In the next step (721) the user or the computer specifies quantity, duration, pressure/flow-rate of the injection, and in (722) the computer predicts the resulting time course of concentration, using the transport parameters established at step (715).

The user or the computer inspects the predicted values and determines (730) whether these are acceptable in the light of the injection goals. If 'No', the procedure returns to step (720), where the instrument position may be readjusted, and defines (721) new values for quantity, duration, pressure/flow-rate of the injection. If 'Yes', the physical procedure begins: if the position was chosen virtually, the instrument must first be placed there physically (740).

Step (740) initiates the injection proper, leading to (745) the first time unit (next after none) of the planned flow. As each time unit is completed a counter tests (750) whether the end of the plan has been reached. If it has, the injection procedure ends (780) with continued monitoring until the transport speed of the injected material has become negligible. If not, the image guidance system monitors the concentration (751) and the computer compares the values with those predicted (760). If disagreement is within a pre-set tolerance, the procedure goes to the next step in the injection plan (745). If it exceeds this tolerance, the computer revises parameter estimates in the light of the new data (761), and makes new predictions with specifications of their confidence level. If these are unacceptable and there is not the time to prepare a satisfactory revised strategy, a test (762) diverts the procedure to end (780). If revision is practical, the user or the computer specifies a modification of the plan (771), computes the results (772) and tests (773) their acceptability. If they are satisfactory, the procedure continues (745) with the revised plan. If not, the system decides (774) whether time is running out. If it is, it goes to the emergency stop subprocess (762). If time is available, the search for an improved plan continues with a return to step (771). These loops continue until the end process (780) is reached.

The method of design of the release of the material from the medical device may be based upon many different release structures or mechanisms. The release may be through actual holes or apertures in a cover for a lumen or on the catheter, membranes on the catheter, open/close stops or blocks on lumens in the catheter, and the like. Each of these different types of systems will provide release or delivery characteristics that should be considered in the analysis of the delivery rate profiles in the practice of the invention.

What is claimed is:

1. A method for the interactive simulation of the movement of a first material in an organism, comprising:
   (a) constructing a field of local physical quantities appropriate to motion, appearance and disappearance of said material in said organism, and
   (b) constructing a field of a rate at which fluid flowing in said organism as a consequence of bodily processes or of an injection process moves at each position, thereby transporting said material, and
   (c) constructing a model of a source from which said material enters said organism, with any pressure differential or flux rate that causes it to enter said organism, and
   (d) computing a concentration field over time of said material, assuming a planned time course of said pressure differential or flux rate, and
   (e) using said concentration field to implement control of concentration of said material by adjustment of the source from which said material enters said organism.

2. The method of claim 1 wherein the field of a rate at which fluid flowing in said organism as a consequence of bodily processes or of an injection process moves at each position is simulated and the field comprises at least one mechanism of movement selected from the group consisting of diffusion, flow, chemical creation or destruction of molecules, and absorption.

3. A method according to claim 2, where said organism is a patient or experimental subject, and said implemented control of the concentration optimizes resulting concentrations in different tissues according to target values therapeutically or scientifically chosen.

4. The method according to claim 3 wherein implemented control comprises minimizing resulting concentrations at tissue that is not targeted for therapy.

5. The method according to claim 4 wherein implemented control also comprises minimizing resulting concentrations at tissue that is not targeted for therapy.

6. The method to claim 3 wherein implemented control optimizes resulting concentrations at tissue targeted for therapy.

7. A method according to claim 2 where a field of diffusion tensor values and of rates of absorption, creation and destruction is constructed from scan data that, by appropriate scaling or other physically calibrated transformation, imply values for concentrations and/or motions of a material that has physical, chemical and biological properties different from those of the first material.

8. A method according to claim 2 where a field of diffusion tensor values and of rates of absorption, creation and destruction is constructed from magnetic resonance data that, by appropriate scaling or other physically calibrated transformation, imply values for concentrations and/or motions of a material that has physical, chemical and biological properties different from those of the first material.

9. A method according to claim 8 where predicted time courses of concentrations under the assumptions of a current plan and of suggested options are graphically displayed by the use of imagery.

10. The method according to claim 9 wherein the user controls a region or slice that displayed by the use of imagery.

11. The method according to claim 10 wherein the user controls optical properties relative to tissue regions and material concentrations are visualized.

12. A method according to claim 2 where the field of of rates of absorption, creation and destruction is constructed, by appropriate scaling or other physically calibrated transformation, from scan data recorded from a previous administration to the specific target region of that organism of material that has physical, chemical and biological properties sufficiently similar to those of the first material to be predictive of its transport properties.

13. A method according to claim 12 where comparison of a predicted concentration with real-time measurement of actual concentration is used to modify the field of local physical quantities to values and rates that predict a continuing change in concentration of said first material, and in pressure and edema.

14. A method according to claim 2 where the field of local physical quantities is constructed from scan data that permit segmentation of a region occupied by said organism into anatomical types, for which anatomical types of regions general diffusion tensor values and absorption rates are known.

15. The method according to claim 14 wherein said general local physical quantities are known from actual measurements on other organisms.

16. A method according to claim 1 where the field of local physical quantities is constructed from scan data that, by scaling or other physically calibrated transformation, imply values for concentrations and/or motions of a material that has physical, chemical and biological properties different from those of the first material.

17. A method according to claim 1 where the field of local physical quantities is constructed, by appropriate scaling or other physically calibrated transformation, from scan data recorded from a previous administration to the specific target region of that organism of material that has physical, chemical and biological properties sufficiently similar to those of the first material to be predictive of its transport properties.

18. A method according to claim 1 where the field of local physical quantities is constructed from scan data that permit segmentation of a region occupied by said organism into anatomical types, for which anatomical types of regions general diffusion tensor values and absorption rates are known.

19. The method according to claim 18 wherein said general diffusion values and absorption rates are known from actual measurements on other organisms.

20. A method according to claim 18 where comparison of a predicted concentration with real-time measurement of actual concentration is used to modify the field of local physical quantities to values and rates that predict a continuing change in concentration of said first material, and in pressure and edema.

21. A method according to claim 1 where the concentration field is computed by solving a finite differential equation constructed from a continuum model of some or all of the processes of transport, absorption, creation and destruction.

22. A method according to claim 21 where the concentration field is computed by the use of a multiplicity of processors acting in parallel, each handling a sub-region of the simulated volume, and using shared or separate memory of the field of local physical quantities.

23. A method according to claim 22 where said multiplicity of processors is embedded on a dedicated chip or assembly of chips are optimized for the computations required after the concentration field is computed.

24. A method according to claim 1 where the concentration field is computed by computing the motion of a number of simulated particles of said first material, with probability of motion in a particular direction controlled by a fluid velocity field and a diffusion tensor field and probability of absorption, creation or destruction controlled by other parts of the field of local physical quantities.

25. A method according to claim 24 where the concentration field is computed by the use of a multiplicity of processors acting in parallel, each processor handling a sub-population of one or more simulated particles, and at least some of said multiplicity of processors using shared or separate memory of the field of local physical quantities.

26. A method according to claim 25 where said computing of the concentration field is performed on a multiplicity of processors is embedded on a dedicated chip or assembly of chips.

27. A method according to claim 24 where a computer explores a range of possible planned time courses for pressure differential or flux rate and identifies certain options as more satisfactory than other planned time courses in terms of predetermined targets, and permits the user to implement an offered time course from among said certain options by an act of assent or selection in a user interface of software embodying the method.

28. A method according to claim 1 where target minimum or maximum concentrations and maximum pressures or extents of edema at particular locations are specified by the user, and a computer warns if said target minima or maxima are predicted to be unmet if a current planned time course of pressure differential or flux rate is executed or continued.

29. The method according to claim 1 wherein said material is a dissolved drug, dispersed drug, emulsified drug, a suspension of cells, or a suspension of nanodevices.

30. A method for the interactive simulation of the movement of a first material in an organism, comprising:
  (a) constructing a field of local physical quantities appropriate to motion, appearance and disappearance of said material in said organism, and
  (b) constructing a field of a rate at which fluid flowing in said organism as a consequence of bodily processes or of an injection process moves at each position, thereby transporting said material, and
  (c) constructing a model of a source from which said material enters said organism, with any pressure differential or flux rate that causes it to enter said organism, and
  (d) computing a concentration field over time of said material, assuming a planned time course of said pressure differential or flux rate, and
  (e) using said concentration field to implement control of concentration of said material by adjustment of the source from which said material enters said organism, where the field of local physical quantities is constructed from magnetic resonance data that, by appropriate scaling or other physically calibrated transformation, imply values for concentrations and/or motions of a material that has physical, chemical and biological properties different from those of the first material to be predictive of its transport properties.

31. A method for providing a plan for the introduction of a first material to the tissue of a patient comprising:

providing an image of an interior volume of a patient, the image having more than one type of bodily composition within a field of view of the image, assigning or determining values for at least two of said more than one type of bodily composition within said field of view, said values relating to at least one property selected from the group consisting of a) solvating ability, b) diffusivity, c) absorptivity, d) adsorptivity, e) degradation, f) production and g) transmissivity for a class of compounds or a specific compound, selecting a position within the field of view for introduction of a first material, selecting a rate of introduction of the first material at said position, determining a pattern of movement over time of first material movement from said position based upon at least the rate of introduction and at least at least one property in said group, comparing said pattern of first material movement to objectives for providing said first material to tissue within said patient, and modifying at least one of a) said position, b) said rate of introduction, c) length of time of first material introduction, and d) physical properties of said first material.

32. A method for providing a plan for the introduction of a first material to the tissue of a patient comprising:

providing an image of an interior volume of a patient, the image having more than one type of bodily composition within a field of view of the image, assigning or determining values for at least two of said more than one type of bodily composition within said field of view, said values relating to at least one property selected from the group consisting of a) solvating ability, b) diffusivity, c) absorptivity, d) adsorptivity, and transmissivity for a class of compounds or a specific compound, selecting a position within the filed of view for introduction of a first material, selecting a rate of introduction of the first material at said position, determining a path of first material movement from said position based upon at least the rate of introduction and at least on of said at least one property, comparing said path of first material movement to objectives for providing said first material to tissue within said patient, and modifying at least one of a) said position, b) said rate of introduction, c) length of time of first material introduction, and d) physical properties of said first material.

\* \* \* \* \*